United States Patent
Wytcherley et al.

(10) Patent No.: US 7,307,188 B2
(45) Date of Patent: Dec. 11, 2007

(54) PURIFICATION OF CARBOXYLIC ACIDS BY COMPLEXATION WITH SELECTIVE SOLVENTS

(75) Inventors: Randi Wright Wytcherley, Belgrade, MT (US); Tai-Li Chou, Bozeman, MT (US)

(73) Assignee: GTC Technology, Inc., Houston, TX (US)

( * ) Notice: Subject to any disclaimer, the term of this patent is extended or adjusted under 35 U.S.C. 154(b) by 319 days.

(21) Appl. No.: 11/102,242

(22) Filed: Apr. 8, 2005

(65) Prior Publication Data

US 2005/0228195 A1 Oct. 13, 2005

Related U.S. Application Data

(60) Provisional application No. 60/561,000, filed on Apr. 9, 2004.

(51) Int. Cl.
*C07C 51/42* (2006.01)
(52) U.S. Cl. ...................................... 562/486
(58) Field of Classification Search .................... None
See application file for complete search history.

(56) References Cited

U.S. PATENT DOCUMENTS

| | | | |
|---|---|---|---|
| 2,636,899 A * | 4/1953 | Burrows et al. | 562/410 |
| 2,849,483 A | 8/1958 | Ham et al. | |
| 2,949,483 A | 8/1960 | Ham et al. | |
| 3,082,250 A | 3/1963 | Baldwin et al. | |
| 4,675,438 A * | 6/1987 | Schwartz et al. | 562/416 |
| 5,492,625 A | 2/1996 | Wytcherley et al. | 224/601 |
| 5,767,311 A | 6/1998 | Lee et al. | 562/487 |
| 5,840,968 A | 11/1998 | Lee et al. | |
| 5,929,274 A | 7/1999 | Lamshing et al. | |
| 6,054,610 A | 4/2000 | Lee et al. | 562/487 |
| 6,140,534 A | 10/2000 | Lee et al. | 562/485 |
| 6,616,831 B1 | 9/2003 | Gentry et al. | 208/313 |
| 6,781,026 B2 | 8/2004 | Lee | 585/864 |
| 2002/0193630 A1 | 12/2002 | Lin et al. | |

FOREIGN PATENT DOCUMENTS

| | | |
|---|---|---|
| GB | 804612 | 11/1958 |
| GB | 818211 | 8/1959 |
| GB | 849189 | 9/1960 |
| GB | 1041046 | 9/1966 |
| GB | 1175877 | 1/1970 |
| GB | 1290981 | 9/1972 |
| WO | 9957090 | 11/1999 |
| WO | 9962857 | 12/1999 |
| WO | WO 2004/009570 | 1/2004 |

* cited by examiner

*Primary Examiner*—Paul A. Zucker
(74) *Attorney, Agent, or Firm*—Wong, Cabello, Lutsch, Rutherford & Brucculeri, LLP

(57) ABSTRACT

A method and apparatus for purifying carboxylic acids is disclosed. A mixture containing crude carboxylic acid is contacted with a selective crystallization solvent to form a slurry of a salt complex of the carboxylic acid and the selective crystallization solvent. The salt complex is recovered and optionally processed to recover the free carboxylic acid. The method and apparatus of the invention is particularly suitable for purifying aromatic dicarboxylic acids such as terephthalic acid. The present invention also reduces contamination by carboxybenaldehyde isomers in crude phthalic acids by oxidizing the carboxybenzaldehyde to the corresponding phthalic acid.

23 Claims, 1 Drawing Sheet

PURIFICATION OF CARBOXYLIC ACIDS BY COMPLEXATION WITH SELECTIVE SOLVENTS

CROSS REFERENCE TO RELATED APPLICATIONS

This application is a non-provisional of Provisional Application Ser. No. 60/561,000, filed Apr. 9, 2004, the entire contents of which are incorporated herein by reference.

STATEMENT OF GOVERNMENT INTEREST

This invention was made with government support under DOE Grant No. DE-FC36-011D14085. As such, the government has certain rights in this invention.

FIELD OF THE INVENTION

The invention relates to the purification of carboxylic acids. More specifically, a method and apparatus for purifying aromatic dicarboxylic acids by complexation and crystallization with a selective crystallization solvent are disclosed.

BACKGROUND OF THE INVENTION

Purified carboxylic acids, and particularly aromatic dicarboxylic acids are industrially important. For example purified terephthalic acid (TPA) is a starting material for the formation of polyester resin, which is, in turn, used to make many materials of commerce having a variety of utilities. Purified terephthalic acid is formed from "crude" terephthalic acid conventionally by a number of purification methods, often with the aid of catalysts. Many of the currently available methods for purifying crude terephthalic acid are not completely satisfactory either from an engineering or an economic standpoint. Yet the purity of terephthalic acid is an important determinant in the formation of polyester resin.

Many of the problems of existing and prior systems for producing purified terephthalic acid stem from the difficulties in economically running reaction systems to produce good yields of crude terephthalic acid, compounded by the difficulties of refining crude terephthalic acid to eliminate impurities and unwanted components to produce purified terephthalic acid of a quality suitable as a starting material for producing polyester. Concomitant problems in prior systems include the high capital investment required for PTA plants, the severity of operating conditions of prior processes, both for the production of crude terephthalic acid, and for its purification, and the need for handling catalyst systems and reaction solvents, as well as reaction byproducts in a way such that environmental problems are minimized, and loss of material is also controlled.

One important factor in the production of purified terephthalic acid is the formation of crystals having a size and shape that provide them with good handling characteristics, washability, and filterability in the PTA manufacturing process, and also provide easier handling and better processability in a polyester process.

U.S. Pat. No. 2,949,483, by Ham et al., describes dissolving terephthalic acid in N-methyl-2-pyrrolidinone then precipitating a "salt complex" containing terephthalic acid and N-methyl-2-pyrrolidinone. The solid is washed with water to remove the N-methyl-2-pyrrolidinone and yield purified TPA. The patent claimed a recovery rate of about 60% to 95% of the weight of the crude terephthalic acid.

U.S. Pat. No. 5,840,968, by Lee, et al., describes a method and apparatus for purifying crude terephthalic acid from a liquid dispersion also containing impurities of unreacted starting materials, solvents, products of side reactions and/or other undesired materials. The method uses the steps of filtering the dispersion to form a crude terephthalic acid filter cake, dissolving the filter cake in a selective crystallization solvent at an elevated temperature to form a solution, crystallizing purified terephthalic acid from the solution in the crystallization solvent by reducing the pressure and temperature of the solution, and separating the crystallized purified terephthalic acid from the solution. The selective crystallization solvent is non-aqueous, non-corrosive and essentially non-reactive with terephthalic acid. Examples of selective crystallization solvents described are N-methyl pyrrolidone or dimethyl acetamide.

U.S. Pat. No. 5,929,274, by Lamshing, et al., describes a method for reducing carboxybenzaldehyde isomers in crude terephthalic and/or isophthalic acids (IPA). Crude TPA or IPA is dissolved in N-methyl pyrrolidone and is subsequently contacted with an oxidant, such as substantially anhydrous hydrogen peroxide, to convert the carboxybenzaldehyde isomer (4-CBA or 3-CBA) to TPA or IPA under moderate temperature and pressure conditions.

U.S. Pat. No. 6,054,610, by Lee et al., describes a method and apparatus for preparing purified terephthalic acid and optionally isophthalic acid from mixed xylenes. The method purifies the oxidation reactor effluent containing a mixture of terephthalic acid and isophthalic acid as well as minor amounts of 4-carboxybenzaldehyde (4-CBA), 3-carboxybenzaldehyde (3-CBA), and toluic acid isomers, to produce purified terephthalic acid and, optionally, purified isophthalic acid in an integrated process.

U.S. Pat. No. 6,140,534, by Lee et al., describes a method for preparing isophthalic acid from metaxylene and especially for purifying crude isophthalic acid (IPA) produced in the course of such method, or otherwise, from a liquid dispersion thereof also containing unreacted starting materials, solvents, products of side reactions and/or other undesired materials. The purifying portion of the method includes the steps of: (1) filtering the dispersion to form a crude IPA filter cake; (2) dissolving the filter cake in a selective crystallization solvent at an elevated temperature to form a solution; (3) crystallizing purified IPA from the solution in the crystallization solvent by reducing the temperature, or pressure, or both of the solution; (4) separating the crystallized purified IPA from the solution; and (5) re-dissolving or soaking the washed purified IPA cake at elevated temperature, to remove the final traces of the crystallization solvent and obtain the desirable particle sizes and shape. The selective crystallization solvent is typically N-methyl pyrrolidone.

SUMMARY OF THE INVENTION

An embodiment of the present invention provides a method and apparatus for purifying carboxylic acid from a mixture containing one or more carboxylic acids and possibly other materials. According to a particular embodiment, the carboxylic acid is terephthalic acid (TPA) and the other materials are starting materials, side products, contaminants, etc., present in the effluent from a terephthalic acid production process. The carboxylic acid is purified by contacting the mixture with a selective crystallization solvent at a temperature and time effective to form a slurry of a salt complex of the carboxylic acid and the selective crystallization solvent; and recovering the salt complex. The salt complex can be used as is or can be further processed to yield the free carboxylic acid. To recover the free acid the salt complex can be decomposed in a selective crystallization solvent in a second crystallization stage and crystallized to yield the free acid.

An embodiment of the present invention also provides a method and apparatus to oxidize partial oxidation products present in the effluent from a terephthalic acid production process, such as carboxybenzaldehydes. An embodiment of the present invention also provides a method and apparatus for separating terephthalic acid and isophthalic acid. These, and other aspects of the invention are enabled by the present disclosure.

DETAILED DESCRIPTION OF THE INVENTION

Figure 1:
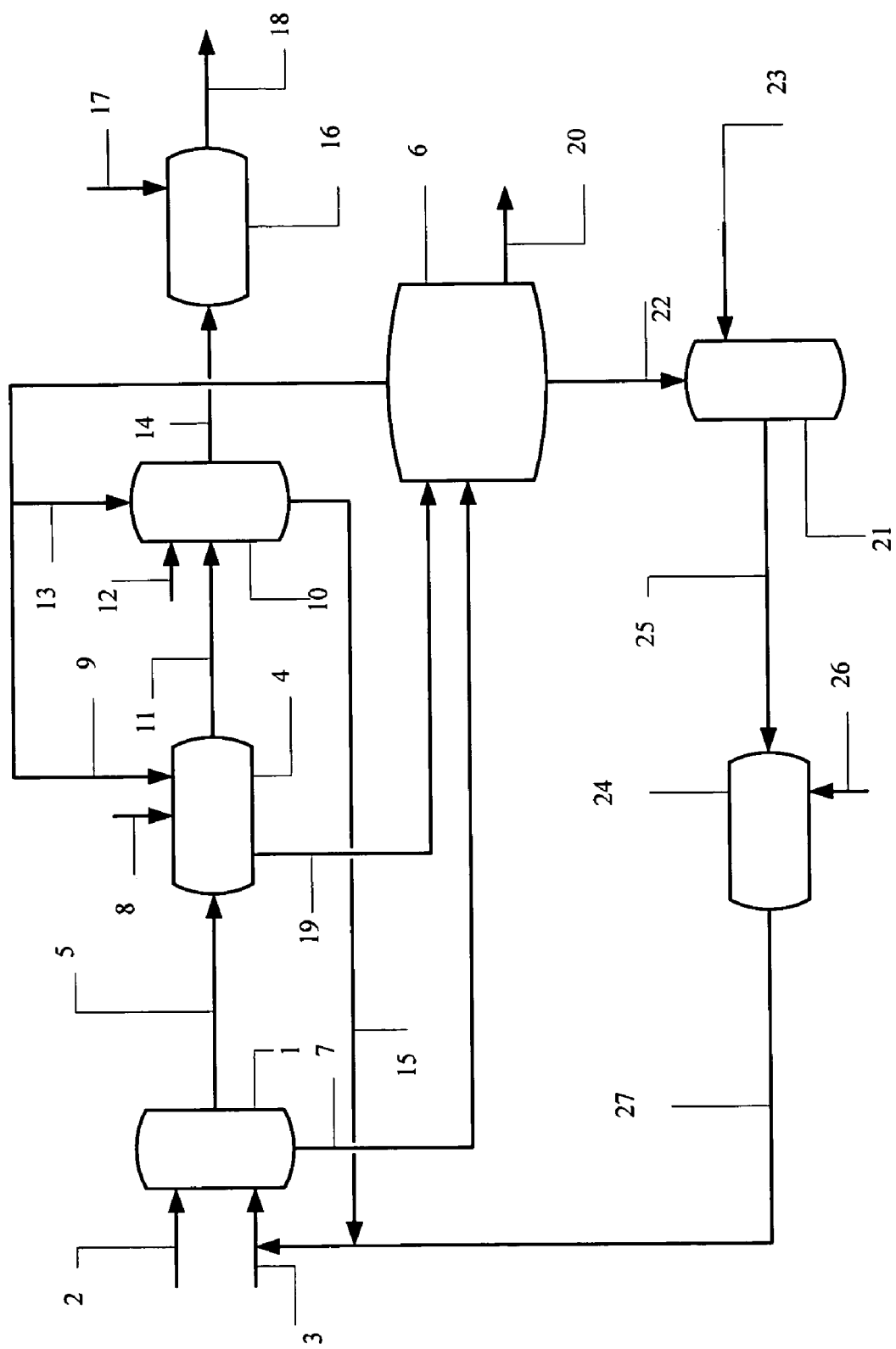
FIG. 1 is a simplified schematic of an embodiment of the invention.

An embodiment of the present invention provides a method of purifying a carboxylic acid from a mixture containing one or more carboxylic acids and possibly other materials. As used herein, purifying means treating the mixture comprising one or more carboxylic acids to yield a composition that is enriched in the desired carboxylic acid compared to the other carboxylic acids and/or other materials that were present in the original mixture. The mixture can be a solid, liquid, or slurry. According to a particular embodiment, the carboxylic acid is a dicarboxylic acid, for example terephthalic acid (TPA), and the other materials are starting materials, side products, contaminants, etc., present in the effluent from a terephthalic acid production process. Alternatively, the carboxylic acid can be isophthalic acid, orthophthalic acid, or other industrially useful carboxylic acids and/or mixtures of these acids.

A number of reaction systems are known for forming crude TPA from a variety of starting materials. The present invention may be used with substantially any of these reaction systems. A common reaction system involves the oxidation of paraxylene (p-xylene). Conventional TPA manufacturing processes require relatively high p-xylene purity (99.7+%) in order to achieve usable quality of product at suitable cost. This is due to the fact that such prior art processes use hydrogenation as the main method for purifying the crude TPA produced in the oxidation section of the processes. Although the hydrogenation method is very selective to eliminate the major impurity, 4-carboxybenzaldehyde (4-CBA) by converting it to p-toluic acid, the method only operates in the presence of a very small amount of 4-CBA (preferably less than 3,000 ppm). Also, the conventional TPA manufacturing processes are not capable of separating TPA from its isomers, such as isophthalic acid (IPA) and phthalic acid (PA).

The present invention provides a method and apparatus for preparing purified TPA and, optionally, isophthalic acid from mixed xylenes. Importantly, the invention can purify oxidation reactor effluent containing terephthalic acid and isophthalic acid as well as minor amounts of 4-carboxybenzaldehyde (4-CBA), 3-carboxybenzaldehyde (3-CBA), and toluic acid isomers, as well as other impurities. The invention produces purified terephthalic acid and optionally purified isophthalic acid in an integrated process. These products are useful for the production of fibers, films, plastic bottles, and polyester resin structures, often reinforced by other materials such as glass fiber.

According to an embodiment of the invention a mixture containing carboxylic acid is contacted with a selective crystallization solvent. As used herein, selective crystallization solvent refers to a solvent that is capable of forming an adduct or a "salt complex" with the carboxylic acid. Exemplary solvents include N,N-dimethyl acetamide, N,N-dimethyl formamide, N-formyl piperidine, N-alkyl-2-pyrrolidone, N-mercaptoalkyl-2-pyrrolidone, N-alkyl-2-thiopyrrolidone, N-hydroxyalkyl-2-pyrrolidone, morpholines, carbitols, $C_1$-$C_{12}$ alcohols, ethers, amines, amides, esters, and mixtures of two or more of these solvents. N-methyl pyrrolidone is a particularly suitable selective crystallization solvent.

U.S. Pat. No. 2,949,483, by Ham et al., the entire contents of which are incorporated herein by reference, describes a method of purifying TPA using N-methyl pyrrolidone. According to Ham, terephthalic acid is completely dissolved in N-methyl-2-pyrrolidinone within the temperature range of 50° C. to 130° C. The solution is cooled to the temperature range of 10° C. to 45° C. and the solid is precipitated. The solid in this case is not terephthalic acid, but is a "salt complex" containing terephthalic acid and N-methyl-2-pyrrolidinone. Ham stated that the salt contains two moles of N-methyl-2-pyrrolidinone for each mole of terephthalic acid. The solid salts formed at low temperature are filtered and washed by N-methyl-2-pyrrolidinone to remove the adhering impurities. The salt is then washed with water between 10° C. to 100° C. Because N-methyl-2-pyrrolidinone is totally miscible with water at all temperatures, the salt is destroyed as the water washes the N-methyl-2-pyrrolidinone from the salt. The remaining terephthalic acid is filtered and dried. Ham states a recovery rate of about 60% to 95% of the weight of the crude terephthalic acid.

Ham's process is not practical for purifying TPA for polyester production. Even if the TPA reaches the desired purity, precipitating, rinsing, filtering, and drying TPA, as described by Ham, are exceedingly difficult. The terephthalic acid crystals formed from these salts are extremely fine, such that the ratio of surface area/volume is too high for efficient drying. These fine crystals form a hard cake or block during filtration. Once a hard cake or block is formed, it is very difficult to process the material further. Even re-dissolving the block in a different solvent presents problems. Due to these disadvantages, this process is not commercially viable.

U.S. Pat. No. 5,767,311, by Lee, et al., the entire contents of which are incorporated herein by reference, describes a multistage crystallization process. In the first crystallizer, crude terephthalic acid is dissolved in N-methyl-2-pyrrolidinone at the temperature range of 140° C. to 190° C., then cooled down to the temperature range of 10° C. to 20° C. to form salts. The salts are filtered and washed with pure N-methyl-2-pyrrolidinone. The salts are then redissolved in N-methyl-2-pyrrolidinone in a second stage crystallizer at a temperature range of 140° C. to 190° C. The solution is cooled to a temperature range of 30° C. to 60° C. to form salts again. The salts are washed with pure N-methyl-2-pyrrolidinone at 45° C. to displace the remaining mother liquor on the surface, and then washed with low-boiling solvent, such as methanol, to break the salts and displace N-methyl-2-pyrrolidinone. The purified terephthalic acid crystals resulting from salts breaking are still fine, but by using a low-boiling solvent instead of water as the wash, the fines are easier to dry, and it is simpler to recover the purified terephthalic acid.

U.S. Pat. No. 6,054,610, by Lee et al., the entire contents of which are incorporated herein by reference, describes additional physical properties of the terephthalic acid-N-methyl-2-pyrrolidinone salt. For example, Lee showed that salts are bright, transparent and slightly pale crystals that can be easily differentiated from the opaque, white terephthalic acid crystals. Lee's empirical molar ratio of N-methyl-2-pyrrolidinone/terephthalic acid in the salt varied from 2.04 to 3.11 instead of 2, as proposed by Ham, because solvent can be trapped in the crystal during the formation of the salt crystals. Lee also showed that with increasing temperature, the salt crystals begin to decompose at about 50° C. This indicates that salts are stable below about 50° C., unstable between 50° C. and 60° C., and terephthalic acid crystals are stable above 60° C. The purification process was further improved based on these observations. According to Lee, crude terephthalic acid is first dissolved in N-methyl-2-pyrrolidinone in a cooling crystallizer between 140° C. to 200° C. The crystallizer is then cooled to a temperature range of 30° C. to 50° C. to achieve good impurities rejection using selective salt formation. The resulting salts are filtered and washed using pure N-methyl-2-pyrrolidinone. The salt slurry is then re-dissolved at the temperature range of 140° C. to 200° C. and fed to a second stage series of flash crystallizers where the temperature and pressure are reduced by steps, with the final temperature being in the range of 50° C. to 60° C. where no salt should be formed. Flash crystallizers are used to produce good crystal shape and size. The purified terephthalic acid crystals are then filtered and washed with pure N-methyl-2-pyrrolidinone and water, and then dried.

A drawback to the method of Lee, described in the preceding paragraph is that the first stage crystallization requires the crude TA to be completely dissolved in the crystallization solvent at an elevated temperature and the second stage crystallization involves a flash crystallization. Both of these stages impart a significant energy burden on the process. An aspect of an embodiment of the present invention is that it does not require as great an energy burden because it does not require complete dissolution of the TA. According to an embodiment of the invention, a mixture containing a carboxylic acid is contacted with a selective crystallization solvent at a temperature and time effective to form a slurry of a salt complex of the carboxylic acid and the selective crystallization solvent. One of skill in the art will appreciate that the fact that a slurry is formed indicates that the salt complex is not completely dissolved in the selective crystallization solvent. According to one embodiment, the salt complex forms via a heterogeneous complexation whereby solid and liquid produce a solid product. The process proceeds at a lower temperature and therefore requires much less externally-added energy than the earlier described processes. For example, the temperature can be any temperature above the melting point of the crystallization solvent and below the temperature at which the salt complex decomposes. According to one embodiment, the temperature can be about 0 to about 65° C. The mixture can be contacted with the selective crystallization solvent for any time period sufficient to allow the salt complex to form. If the kinetics of salt complex formation is very fast, then contacting the mixture with the crystallization solvent instantaneously or for a matter of seconds may be sufficient. Alternatively, the mixture can be contacted with the crystallization solvent for a longer period of time, for example about 30 seconds to about 24 hours, or about 1 minute to about 5 hours. If the mixture containing the carboxylic acid is a solid or a slurry, it may be desirable to process the solid or slurry to produce small particle sizes, prior to contacting the mixture with the selective crystallization solvent. For example, the solid or crude slurry can be ground or agitated to produce particles having small size.

According to an embodiment of the invention, the salt complex is recovered, for example by filtration to yield a filter cake containing the salt complex and a mother liquor containing solvent and possibly excess crude carboxylic acid, starting materials, impurities, etc. According to one embodiment, the salt complex of the carboxylic acid so recovered can be used without further processing or with minimal further processing such as rinsing with solvent, drying etc. Some industrially relevant processes will tolerate the salt complex of the carboxylic acid as feed stock in lieu of the free carboxylic acid. For example, if a polyester process has a high tolerance for the solvent used to purify TA, the TA salt complex may be added directly to the polyester process without recovering the free TA.

Alternatively, the salt complex can be further processed to recover the free carboxylic acid. For example, the salt complex can be crystallized in one or more second crystallization stages to yield free carboxylic acid. According to an embodiment of the invention, the filter cake containing the salt complex is decomposed in a selective crystallization solvent. According to one embodiment, the salt complex is essentially completely dissolved during this second crystallization stage (and any following second crystallization stages, if they are present). The temperature of the second crystallization stage(s) is typically higher than that of the first stage crystallization, to promote complete dissolution of the salt complex. The temperature for the second crystallization stage(s) can be any temperature at which the salt complex dissolves, but the final temperature should be above the temperature at which the salt complex decomposes, so that the free carboxylic acid is obtained. Alternatively, the salt complex can be decomposed without completely dissolving the salt complex, i.e., via a heterogeneous process in a slurry of the salt complex. According to one embodiment, the temperature of the second crystallization can be about 65 to about 300° C. Alternatively, the temperature can be about 65 to about 200° C. Alternatively, the temperature can be about 65 to about 150° C.

Crystallization of free carboxylic acid from the second crystallization stage(s) can be achieved, for example by lowering the temperature of the slurry or solution and/or reducing the volume of solvent. When lowering the temperature, it is desirable that the temperature remain above the temperature at which the salt complex decomposes. For example, the temperature can be reduced to about 60 to about 185° C., alternatively to about 60 to about 100° C. The volume of the solvent can be reduced, for example, by vacuum or by passing an inert gas stream, such as nitrogen, over or through the solvent. Alternatively, the free carboxylic acid can be crystallized by adding an anti-solvent to the second crystallization stage(s). Examples of suitable anti-solvents include water, methanol, ethanol and other alcohols, acids, amines, ethers and aromatics.

It may be desirable to provide external energy to the second crystallization stage(s), for example by stirring or agitation, so that the desirable crystal morphology of the free carboxylic acid is obtained. For example, desirable processability in polyester manufacturing requires TA crystals be robust, have good flow properties, and be of a size such that subsequent dissolution can be easily achieved. In general, both robustness and good flow properties are characteristics of crystals that are spherical or globular instead of bar or needle shaped. As used herein, the term "globular" will refer to crystals that have good flow properties and robustness. The term globular does not limit the crystal to any particular aspect ratio and may encompass crystals that are spherical, oblong, potato shaped, as opposed to needle or bar shaped.

The free carboxylic acid crystallized during the second crystallization stage(s) can be collected, for example by filtering to yield a filter cake containing the free carboxylic acid. For example, if the carboxylic acid is TPA, the filter cake obtained from the second crystallization stage(s) contains purified TPA. This filter cake can be recovered at this point or washed/recrystallized from water or another solvent as described below. From this point on, the purified TPA is manageable to handle because of the desirable crystal morphology obtained by the second crystallization stage(s).

According to an alternative embodiment, the carboxylic acid is a mixture of terephthalic acid and one or more other acids such as isophthalic acid. An embodiment of the invention includes a process for separating terephthalic acid from isophthalic acid and/or other carboxylic acids. A process for separating terephthalic acid and isophthalic acid is described in U.S. Pat. No. 6,054,610, by Lee et al., the entire contents of which are incorporated herein by reference. Briefly, the second crystallization stage(s) are further subdivided into an early stage wherein TPA is selectively crystallized and recovered and isophthalic acid and/or other acids are crystallized from the remaining TPA-depleted solution in one or more successive crystallization step(s). According to an alternative embodiment, the mother liquor that is provided by recovering the salt complex, as describe above, contains terephthalic acid and isophthalic acid. According to one embodiment, terephthalic acid can be precipitated from the mother liquor to yield a terephthalic acid-depleted stream and then isophthalic acid can be precipitated from the terephthalic acid-depleted stream.

The filter cake containing free carboxylic acid from the second crystallization stage(s) can be washed with a suitable solvent to remove any adhering crystallization solvent and to facilitate drying of the solvent. Suitable solvents for washing include water, methanol, ethanol and other alcohols, acids amines, ethers and aromatics. A particularly suitable rinsing solvent is water. The rinsing can involve briefly washing the free acid with the rinsing solvent, soaking the free acid, or even completely dissolving the free acid in the rinsing solvent and crystallizing the free acid there from.

Conventional TPA manufacturing processes require relatively high p-xylene purity (99.7+%) because these processes typically employ hydrogenation as the main method for purifying the crude TPA. Although the hydrogenation method is very selective to eliminate the major impurity, 4-carboxybenzaldehyde (4-CBA) by converting it to p-toluic acid, the method only operates in the presence of a very small amount of 4-CBA (preferably less than 3,000 ppm). An embodiment of the present invention provides a method for purifying the oxidation reactor effluent containing minor amounts of 4-carboxybenzaldehyde (4-CBA), 3-carboxybenzaldehyde (3-CBA), and toluic acid isomers by incorporating a CBA oxidation step in the process stream. According to this embodiment, an oxidant is added to the mother liquor or a portion of the mother liquor obtained by filtering the effluent from the salt complex crystallization, which typically contains some amount of CBA. The oxidizing step allows a portion of this CBA to be oxidized to the dicarboxylic acid and the mother liquor to be recycled back to the salt complex crystallization stage, thereby increasing the overall efficiency of the process. It may be desirable to adjust the concentration of CBA in the mother liquor that is oxidized, for example by purging a portion of the mother liquor and recycling a portion of the mother liquor, so that the concentration of CBA in the remaining mother liquor remains within a desirable concentration range. According to an embodiment, pure solvent can be distilled from the mother liquor to concentrate the impurities. Optionally, impurities in the concentrated mother liquor can be precipitated and recycled to the first crystallizer. According to an embodiment of the invention, the CBA range in the concentrated mother liquor is maintained between about 100 ppm and about 50%, preferably between about 1 and about 10%, and most preferably about 5%.

Examples of suitable oxidants include air, enriched air, pure oxygen, hydrogen peroxide, aqueous hydrogen peroxide, hydrogen peroxide in an organic liquid, ozone, carbon tetrachloride, trichloroacetaldehyde, hexamine, acetone, cyclohexanone, benzophenone, cinnamaldehyde, dimethyl sulfoxide, sulfides, chiral oxidants, glyoxals, organic peroxy acids, such as performic acid, peracetic acid, perbenzoic acid, perpropionic acid, permaleic acid, and perphthalic acid. According to one embodiment, the pH of the CBA oxidation step is about −2 to about 6, preferably about −1 to about 4, and even more preferably −1 to about 2.1. The pH of the CBA oxidation can be adjusted with an organic or inorganic acid. Examples of suitable acids include chromic acid, hydroflouric acid, iodic acid, hydrochloric acid, sulfuric acid, nitric acid, selenic acid, picric acid, trinitrophenol (2,4,6-) acid, napthalenesulfonic acid, benzosulfonic acid, trichloroacetic acid, oxalic acid, dichloroacetic acid, trihydroxybenzoic (2,4,6-) acid, cyclopropane-1:1-dicarbozylic acid, acetic acid, maleic acid, dihydroxymalic acid, dihydroxytartaric acid, dichloroacetylacetic acid, lutidinic acid, o-nitrobenzoic acid, γ-cyanobutyric acid, cyanopropionic acid, cyanoacetic acid, o-aminobenzosulfonic acid, quinolinic acid, bromoacetic acid, dinicotinic acid, α-chloropropinic acid, malonic acid, o-bromobenzoic acid, chloroacetic acid, o-iodobenzoic acid, α-chlorobutyric acid, o-phthalic acid, flurobenzoic acid, o-chlorobenzoic acid, p-cyanophenoxyacetic acid, dihydroxybenzoic (2,2-) acid, formic acid, dihydroxybenzoic (2,5-) dcid, o-hydroxybenzoic acid, o-cyanophenoxyacetic acid, and α-tartaric acid.

An embodiment of the present invention is an apparatus for implementing the process described above. A simplified schematic of such an apparatus is depicted in FIG. 1. It should be understood that pipelines are in fact being designated when streams are identified and that streams are intended, if not stated, when materials are mentioned. Moreover, flow control valves, temperature regulator devices, pumps, compressors, and the like are understood as installed and operating in conventional relationships to the major items of equipment which are shown in the drawings and discussed hereinafter with reference to the continuously operating process of this invention. All of these valves, devices, pumps, and compressors, as well as heat exchangers, accumulators, condensers and the like, are included in the term "auxiliary equipment". It is in the ability of one of ordinary skill in the art to implement such auxiliary equipment, as needed, in view of the present disclosure.

Referring to FIG. 1, a mixture containing crude carboxylic acid is provided to vessel 1 via stream 2 and a selective crystallization solvent is provided via stream 3. Vessel 1 can be any suitable vessel known in the art. Vessel 1 preferably contains a stage for contacting the mixture containing carboxylic acid with a selective crystallization solvent to form a slurry of the salt complex and a means for separating the salt complex from the mother liquor. Alternatively, these two functions can be performed by multiple pieces of equipment. The salt complex is transferred to vessel 4 via stream 5 and the mother liquor is transferred to vessel 6 via stream 7. The salt complex is rinsed in vessel 4 with saturated selective crystallization solvent that is provided via stream 8 and/or pure selective crystallization solvent that is provided via stream 9. In the depicted embodiment, pure solvent is provided as recycled solvent from vessel 6. Alternatively, the solvent could be added from an external source, for example, as make-up solvent.

The salt complex is transferred to vessel 10 via stream 11, where it is dissolved in selective crystallization solvent. Selective crystallization solvent already containing salt complex, and optionally other solvents, can be provided via stream 12. Pure selective crystallization solvent is provided via stream 13. In the depicted embodiment, pure solvent is provided as recycled solvent from vessel 6. Alternatively, the solvent could be added from an external source, for example, as make-up solvent. The temperature of the contents of vessel 10 is maintained such that essentially the entire salt complex decomposes or dissolves. According to one embodiment, the temperature of the contents of vessel 10 can be about 65 to about 300° C. The temperature of vessel 10 can be decreased and/or the volume of solvent present in vessel 10 can be decreased or a non-solvent added to vessel 10 to facilitate the crystallization of free carboxylic acid. For example, the volume of solvent can be decreased by passing a stream of inert gas, e.g., $N_2$, over the surface or through the solution. Likewise, the temperature can be decreased, but preferably the temperature remains above the temperature at which the salt complex decomposes. For example, the temperature can be reduced to about 60 to about 100° C. According to one embodiment, energy is added to vessel 10, for example by stirring or agitation. Preferably, the energy is such that the free carboxylic acid crystals that are formed are globular, i.e., have desired flow and processability characteristics. Vessel 10 can be any suitable vessel known in the art and preferably provides a means of dissolving the salt complex in the solvent, stirring the solution to provide adequate energy to yield the desirable crystal size and shape, recovering the solid free acid crystals, and optionally providing additional solvents or anti-solvents. These functions can all be performed using one piece of equipment or multiple pieces of equipment. FIG. 1 depicts an apparatus having one second crystallization vessel 10, but an alternative embodiment is an apparatus having multiple second crystallization stages.

Selective crystallization solvent is recycled to the first crystallization vessel 1 via stream 15 or optionally recycled to first rinse vessel 4 or optionally can be sent to vessel 6 for solvent recovery. The recovered free acid is transferred to vessel 16, where it is rinsed with a one or more rinsing solvents provided via stream 17. The depicted embodiment shows stream 17 being provided from an external source, but solvent can also be provided as recycled solvent from vessel 6. The free carboxylic acid can be rinsed by briefly contact with the rinsing solvent, by more lengthy contact or soaking in the rinsing solvent, or by dissolving the free acid in the rinsing solvent and crystallizing the free acid there from. Free acid obtained from the rinsing stage exits the process via stream 18. Rinsing solvents from vessel 16 may optionally be recovered in vessel 6 or recycled to vessel 1 or optionally recycled to vessel 4.

Mother liquor from vessel 1 is transferred to vessel 6 via stream 7 and selective crystallization solvent from vessel 4 is transferred to vessel 6 via stream 19. The contents of vessel 6 therefore contains selective crystallization solvent and likely one or more of crude free acid, starting material, partial oxidation products and side products from the acid formation process, and possibly other contaminants. In an embodiment of the invention used as a purification for TPA prepared from the oxidation of p-xylene (or mixed xylenes) the primary partial oxidation products are 4-carboxybenzaldehyde (4-CBA), 3-carboxybenzaldehyde (3-CBA, derived from m-xylene), and toluic acid isomers, with 4-CBA likely being dominant. In such an embodiment, the concentration of partial oxidation product can be adjusted by varying the amount of pure solvent recovered from vessel 6 (as more pure solvent is recovered, the impurities become more concentrated in the concentrated mother liquor). To allow for a material balance, an amount of concentrated mother liquor from vessel 6 can be purged via purge stream 20. The remaining concentrated mother liquor is transferred to vessel 21 via stream 22. According to one embodiment, some of the contents of stream 22 may tend to precipitate. According to one embodiment, such precipitants can be removed from stream 22 or recycled, for example, to vessel 1. The pH of the contents of vessel 21 can optionally be adjusted by adding pH adjusting reagent via stream 23. Suitable pH adjusting reagents include acids such as organic and inorganic acids, for example, chromic acid, hydroflouric acid, iodic acid, hydrochloric acid, sulfuric acid, nitric acid, selenic acid, picric acid, trinitrophenol (2,4,6-) acid, napthalenesulfonic acid, benzosulfonic acid, trichloroacetic acid, oxalic acid, dichloroacetic acid, trihydroxybenzoic (2,4,6-) acid, cyclopropane-1:1-dicarbozylic acid, acetic acid, maleic acid, dihydroxymalic acid, dihydroxytartaric acid, dichloroacetylacetic acid, lutidinic acid, o-nitrobenzoic acid, γ-cyanobutyric acid, cyanopropionic acid, cyanoacetic acid, o-aminobenzosulfonic acid, quinolinic acid, bromoacetic acid, dinicotinic acid, α-chloropropinic acid, malonic acid, o-bromobenzoic acid, chloroacetic acid, o-iodobenzoic acid, α-chlorobutyric acid, o-phthalic acid, flurobenzoic acid, o-chlorobenzoic acid, p-cyanophenoxyacetic acid, dihydroxybenzoic (2,2-) acid, formic acid, dihydroxybenzoic (2,5-) acid, o-hydroxybenzoic acid, o-cyanophenoxyacetic acid, and α-tartaric acid. Acids used to adjust the pH can optionally be recovered and recycled from stream 27. The contents of vessel 21 are transferred to vessel 24 via stream 25. The contents of vessel 24 are oxidized with oxidant provided via stream 26 and then transferred to vessel 1 via stream 27. Suitable oxidants include air, enriched air, pure oxygen, hydrogen peroxide, aqueous hydrogen peroxide, hydrogen peroxide in an organic liquid, ozone, carbon tetrachloride, trichloroacetaldehyde, hexamine, acetone, cyclohexanone, benzophenone, cinnamaldehyde, dimethyl sulfoxide, sulfides, chiral oxidants, glyoxals, organic peroxy acids, such as performic acid, peracetic acid, perbenzoic acid, perpropionic acid, permaleic acid, and perphthalic acid. Oxidants and oxidation by-products can optionally be recovered and recycled from stream 27.

EXAMPLES

Example 1

4-CBA Rejection Using Salt Complex Purification

Slurries were produced by adding 28 g crude TA (containing 2.5% 4-CBA) to 100 g of NMP in three beakers. The three slurries were maintained at about 41-46° C. while mixing. The samples were filtered and rinsed with saturated PTA/NMP solution at 40° C. 4-CBA concentrations were determined by Gas Chromatography. The results are shown in Table 1.

TABLE 1

4-CBA rejection by salt complex purification for various mixing times.

| Mixing time (min) | 4-CBA conc. (wt %) | 4-CBA rejection |
|---|---|---|
| 15 | 0.131 | 94.8% |
| 30 | 0.104 | 95.8% |
| 45 | 0.095 | 96.2% |

Example 2

4-CBA Rejection Using Salt Complex Purification at Various Temperatures

Slurries were produced by adding 28 g crude TA (containing 2.5% 4-CBA) to 100 g of NMP in three beakers while mixing for 30 minutes. The three slurries were maintained at constant temperatures while mixing. Each sample was then filtered and rinsed with saturated PTA/NMP solution at its temperature. 4-CBA concentrations were determined by Gas Chromatography. The results are shown in Table 2.

TABLE 2

4-CBA rejection by salt complex formation at various temperatures.

| Salt formation temperature (° C.) | 4-CBA conc. (wt %) | 4-CBA rejection |
|---|---|---|
| 26-28 | 0.138 | 94.5% |
| 34-35 | 0.138 | 94.5% |
| 52-56 | 0.107 | 95.7% |

Example 3

4-CBA Oxidation at Various pHs

This example illustrates the effect of pH on the oxidation process of 4-CBA with $H_2O_2$. Oxidation was conducted at 25° C. for 300 minutes. The results are shown in Table 3. The results indicate that lowering the pH yields significantly greater oxidation.

TABLE 3

4-CBA oxidation at various pH.

| 4-CBA conc. (wt %) | $H_2O_2$ conc. (wt %) | pH | 4-CBA conversion |
|---|---|---|---|
| 3.89 | 2.31 | 2.1 | 5% |
| 3.88 | 2.14 | −0.4 | 72% |

What is claimed is:

1. A method of purifying a carboxylic acid from a crude mixture comprising one or more carboxylic acids, the method comprising:
   contacting the crude mixture with a selective crystallization solvent at a temperature and time effective to form a slurry of a salt complex of the carboxylic acid and the selective crystallization solvent without completely dissolving the carboxylic acid; and
   recovering the salt complex.

2. The method of claim 1, wherein the carboxylic acid is selected from the group consisting of terephthalic acid, isophthalic acid, orthophtalic acid, and mixtures thereof.

3. The method of claim 1, wherein the selective crystallization solvent is selected from the group consisting of N,N-dimethyl acetamide, N,N-dimethyl formamide, N-formyl piperidine, N-alkyl-2-pyrrolidone, N-mercaptoalkyl-2-pyrrolidone, N-alkyl-2-thiopyrrolidone, N-hydroxyalkyl-2-pyrrolidone, morpholines, carbitols, $C_1$-$C_{12}$ alcohols, ethers, amines, amides, esters, and mixtures thereof.

4. The method of claim 1, wherein the selective crystallization solvent is N-methyl pyrrolidone.

5. The method of claim 1, wherein the temperature is about 0 to about 65° C.

6. The method of claim 1, wherein the time is about 1 minute to about 5 hours.

7. The method of claim 1, further comprising decomposing the salt complex in a selective crystallization solvent to provide free carboxylic acid.

8. The method of claim 7, wherein the salt complex is dissolved in the selective crystallization solvent.

9. The method claim 7, wherein the salt complex forms a slurry in the selective crystallization solvent.

10. The method of claim 7, further comprising stirring the selective solvent with energy sufficient to provide crystallization of the carboxylic acid having globular crystal shape.

11. The method of claim 7, further comprising reducing the temperature of the selective solvent.

12. The method of claim 7, further comprising reducing the volume of the selective solvent by evaporating a portion of said selective crystallization solvent.

13. The method of claim 7, further comprising adding a non-solvent to the selective crystallization solvent.

14. The method of claim 1, wherein the mixture further comprises one or more materials selected from the group consisting of carboxybenzaldehyde, toluic acid, and xylene; and wherein recovering the salt complex yields a mother liquor that is enriched in one or more of the materials, the method further comprising adding an oxidant to a portion of the mother liquor.

15. The method of claim 14, wherein the oxidant is selected from the group consisting of air, enriched air, pure oxygen, hydrogen peroxide, aqueous hydrogen peroxide, hydrogen peroxide in an organic liquid, ozone, carbon tetrachloride, trichloroacetaldehyde, hexamine, acetone, cyclohexanone, benzophenone, cinnamaldehyde, dimethyl sulfoxide, sulfides, chiral oxidants, glyoxals, organic peroxy acids, such as performic acid, peracetic acid, perbenzoic acid, perpropionic acid, permaleic acid, and perphthalic acid.

16. The method of claim 14, wherein the pH of said portion of the mother liquor is about −1 to about 7.

17. The method of claim 14, wherein the pH of said portion of the mother liquor is adjusted to −1 to about 7 by adding acid to said mother liquor.

18. The method of claim 14, further comprising purifying additional carboxylic acid from said portion by contacting said portion with a selective crystallization solvent at a temperature and time effective to form a slurry of a salt complex of the additional carboxylic acid and the selective crystallization solvent and recovering the salt complex.

19. The method of claim 1, wherein the mixture comprises terephthalic acid and isophthalic acid and wherein recovering said salt complex yields a mother liquor, the method further comprising precipitating terephthalic acid from the mother liquor to yield a terephthalic acid-depleted stream and then precipitating isophthalic acid from the terephthalic acid-depleted stream.

20. The method of claim 7, wherein the mixture comprises terephthalic acid and isophthalic acid, the method further comprising reducing the temperature and volume of the second crystallization solvent or adding a non-solvent to the second crystallization in a first stage to selectively recover free terephthalic acid and to produce a terephthalic acid-depleted solution and then reducing the temperature and volume of the terephthalic acid-depleted solution in a second stage to selectively recover isophthalic acid.

21. The method of claim 1, wherein the carboxylic acid is selected from the group consisting of terephthalic acid, isophthalic acid, orthophtalic acid, and mixtures thereof; wherein the mixture further comprises one or more materials selected from the group consisting of carboxybenzaldehyde, toluic acid, and xylene; wherein recovering said salt complex yields a mother liquor that is enriched in one or more of said materials; and wherein the selective crystallization solvent is selected from the group consisting of N,N-dimethyl acetamide and N-methyl pyrrolidone, the method further comprising: decomposing or dissolving said salt complex in a selective crystallization solvent to form a second slurry or solution and precipitating the free carboxylic acid from said second solution while agitating said second solution with energy sufficient to provide crystallization of the carboxylic acid having globular crystal shape, and adding an oxidant to said mother liquor, wherein the oxidant is selected from the group consisting of air, enriched air, pure oxygen, hydrogen peroxide, aqueous hydrogen peroxide, hydrogen peroxide in an organic liquid, ozone, carbon tetrachloride, trichloroacetaldehyde, hexamine, acetone, cyclohexanone, benzophenone, cinnamaldehyde, dimethyl sulfoxide, sulfides, chiral oxidants, glyoxals, organic peroxy acids, such as performic acid, peracetic acid, perbenzoic acid, perpropionic acid, permaleic acid, and perphthalic acid.

22. A method for recovering purified terephthalic acid from the effluent of a terephthalic acid production process, the method comprising:

contacting said effluent in a first crystallization vessel with a selective crystallization solvent to produce a slurry of a salt complex of terephthalic acid and the crystallization solvent without completely dissolving the terephthalic acid in the selective crystallization solvent;

filtering said slurry to provide a solid salt complex and a mother liquor;

decomposing or dissolving the solid salt complex with a selective crystallization solvent in a second crystallization vessel at a temperature of about 65 to about 300° C. to yield a second crystallization slurry or solution;

reducing the temperature of the second crystallization solution to about 60 to about 185° C. to crystallize free terephthalic acid; and recovering the free terephthalic acid.

23. The method of claim 19, further comprising adjusting the pH of a portion of the mother liquor to about −1 to about 7 and adding an oxidant to said portion of the mother liquor, wherein the oxidant is selected from the group consisting of air, enriched air, pure oxygen, hydrogen peroxide, aqueous hydrogen peroxide, hydrogen peroxide in an organic liquid, ozone, carbon tetrachloride, trichloroacetaldehyde, hexamine, acetone, cyclohexanone, benzophenone, cinnamaldehyde, dimethyl sulfoxide, sulfides, chiral oxidants, glyoxals, organic peroxy acids, such as performic acid, peracetic acid, perbenzoic acid, perpropionic acid, permaleic acid, and perphthalic acid; and recycling said portion of the mother liquor to the first crystallization vessel.

* * * * *